United States Patent
Walston et al.

[11] Patent Number: 5,879,396
[45] Date of Patent: *Mar. 9, 1999

[54] JOINT PROSTHESIS HAVING PTFE CUSHION

[76] Inventors: D. Kenneth Walston, 4585 N. Sugarbush Pl., Tucson, Ariz. 85749; Lawrence M. Haas, 5468 Gleneagles Dr., Tucson, Ariz. 85718

[ * ] Notice: The term of this patent shall not extend beyond the expiration date of Pat. No. 5,507,823.

[21] Appl. No.: 845,346

[22] Filed: Apr. 25, 1997

Related U.S. Application Data

[63] Continuation of Ser. No. 608,538, Feb. 28, 1996, abandoned, which is a continuation-in-part of Ser. No. 306,725, Sep. 15, 1994, Pat. No. 5,507,823, which is a continuation-in-part of Ser. No. 173,979, Dec. 28, 1993, abandoned.

[51] Int. Cl.⁶ ........................................................ A61F 2/42
[52] U.S. Cl. ................................ 623/21; 623/16; 623/18; 623/20
[58] Field of Search ................................. 623/16, 18, 20, 623/21

[56] References Cited

U.S. PATENT DOCUMENTS

| | | | |
|---|---|---|---|
| 3,745,590 | 7/1973 | Stubstad | 3/1 |
| 4,158,893 | 6/1979 | Swanson | 623/21 |
| 4,280,500 | 7/1981 | Ono | 128/348 |
| 4,313,232 | 2/1982 | Habal et al. | 3/1.91 |
| 4,531,916 | 7/1985 | Scantlebury et al. | 433/173 |
| 4,576,608 | 3/1986 | Homsy | 623/11 |
| 4,919,668 | 4/1990 | Rosenbaum et al. | 623/18 |
| 5,011,497 | 4/1991 | Persson et al. | 623/51 |
| 5,049,155 | 9/1991 | Bruchman et al. | 623/17 |
| 5,062,851 | 11/1991 | Branemark | 623/18 |
| 5,067,964 | 11/1991 | Richmond et al. | 623/18 |
| 5,098,779 | 3/1992 | Kranzler et al. | 428/306.6 |
| 5,480,447 | 1/1996 | Skiba | 623/21 |
| 5,491,882 | 2/1996 | Walston et al. | 29/419.1 |
| 5,507,823 | 4/1996 | Walston et al. | 623/21 |

FOREIGN PATENT DOCUMENTS 0454645  10/1991  European Pat. Off. .

*Primary Examiner*—Paul B. Prebilic
*Attorney, Agent, or Firm*—Cahill, Sutton & Thomas, P.L.C.

[57] ABSTRACT

A joint prosthesis for interconnecting the ends of adjoining bones includes a cushion of expanded PTFE having at least two facets for attachment to the bones. The cushion may or may not include stems for insertion into the bones. An optional sheath surrounds the non-facet surfaces of the cushion for preventing adherence of tissue. The motion of the prosthesis is defined or limited by the orientation of the facets and/or by the porosity of the cushion and/or by an insert within the cushion.

5 Claims, 3 Drawing Sheets

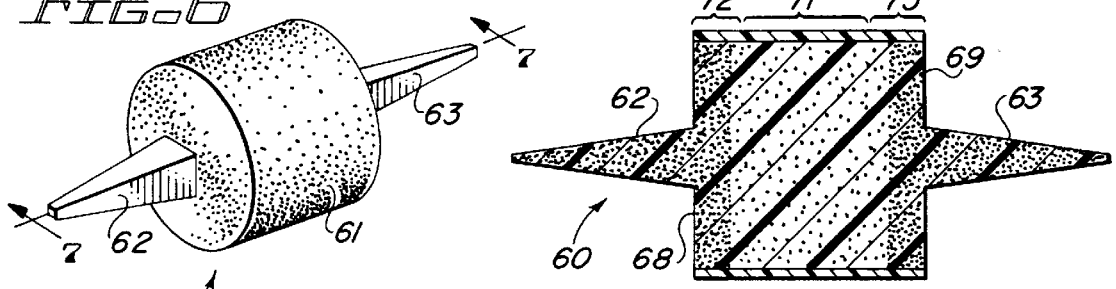
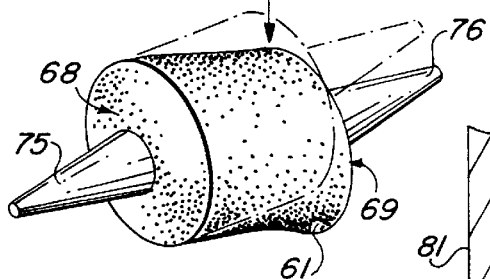
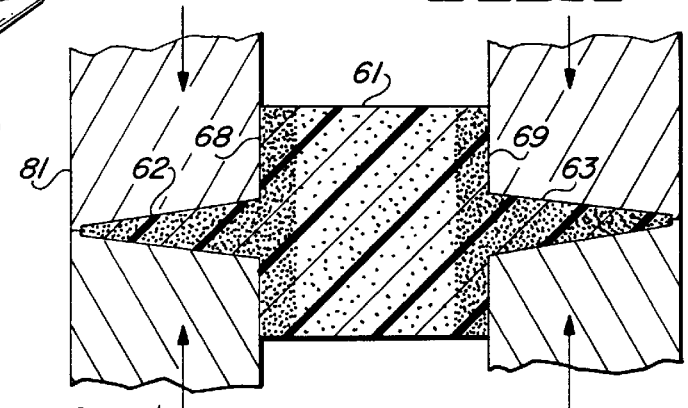
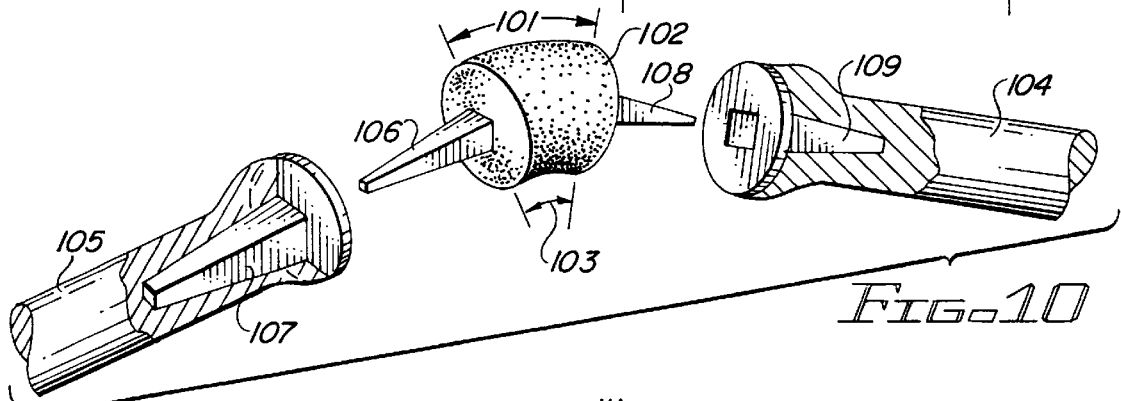
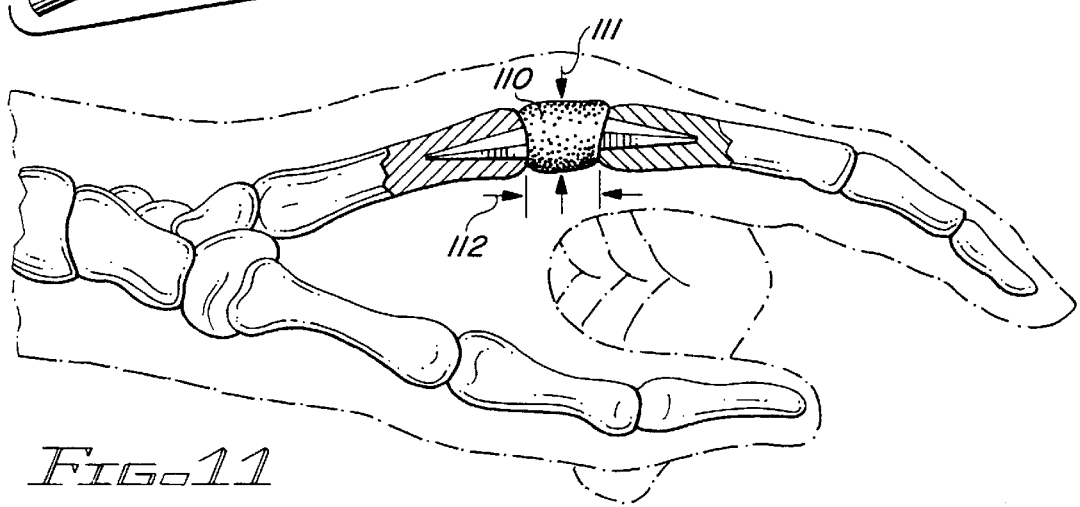

JOINT PROSTHESIS HAVING PTFE CUSHION

CROSS-REFERENCE TO RELATED APPLICATIONS

This application is a file wrapper continuation of patent application Ser. No. 08/608,538, filed on Feb. 28, 1996, now abandoned, which was a continuation of patent application Ser. No. 08/306,725, filed on Sep. 15, 1994, which issued as U.S. Pat. No. 5,507,823 on Apr. 16, 1996; in turn, patent application Ser. No. 08/306,725 was a file wrapper continuation of patent application Ser. No. 08/173,979, filed on Dec. 28, 1993, now abandoned.

In addition, applicants filed a divisional patent application Ser. No. 08/304,935, filed Sep. 13, 1994, based upon the aforementioned patent application Ser. No. 08/173,979, filed on Dec. 28, 1993; such divisional patent application Ser. No. 08/304,935 later issued as U.S. Pat. No. 5,491,882 on Feb. 20, 1996.

BACKGROUND OF THE INVENTION

This invention relates to reconstructed joints between bones and, in particular, to an improved prosthetic joint having a mass of expanded PTFE as the articulating, connective material.

In current medical practice, a joint severely afflicted with disease or injury is replaced with one of a variety of prostheses. One type of prosthesis includes metal socket elements which are shaped similarly to the adjoining ends of healthy bones and have stems for insertion into bones. This type of prosthesis is used for a joint subjected to heavy loads, such as the hip joint. Another type of prosthesis, typically used for replacing damaged joints between bones subjected to minimal loads, includes an elastomer hinge for coupling the bones. This type of prosthesis is less expensive than the first type and is more suited for smaller joints, e.g. the metacarpophalangeal (MCP) joints in the second through fifth fingers.

It is desired to restore the integrity and functionality of a joint as much as possible. For joints normally having limited motion, this goal is relatively easily attained. For joints capable complicated motions, such as the bi-axial motion of the fingers, this goal becomes far more difficult. The bi-axial motion of a thumb is readily demonstrated by placing a hand flat upon a flat surface. Moving the thumb toward the palm (adduction) or away from the palm (abduction) while the thumb rests on the surface is motion about one axis and moving the thumb up from the surface (extension) or into the surface (flexion) is motion about the second axis.

Movement about two axes can be achieved with mechanical prostheses but these are often too expensive and of limited reliability. Prostheses made with elastomer hinges either do not provide bi-axial motion or permit unnatural motion of the bones. Either type of prosthesis in the prior art provides a hinge or swinging kind of motion, not the sliding motion of a natural joint.

Mechanical, i.e. metal, joints are often fastened to the bones with a bone adhesive. However, the mechanical joints are not resilient and the shock transmitted to the joint often causes the adhesive layer to crack or to remove a thin, adherent layer of bone tissue. In addition, the bone adhesive deteriorates with time. As a result, the joint must eventually be repaired or replaced.

Elastomer hinges have the advantage of being resilient but are rapidly falling into disfavor because they are typically made from silicone, which has been found to be incompatible with the tissue surrounding an implant. Silicone can break down into small particles that are ingested by body cells, causing an inflammation known as "silicone synovitis". The flexible web connecting the two halves of the hinge can fracture from repeated use and the whole prosthesis may have to be replaced. Also, silicone in prolonged contact with bone can cause the bone to dissolve.

All known prostheses currently used have limited life in the patient before the problems described above begin to appear, sometimes as soon as one year after a joint is replaced. A problem that occurs immediately upon replacement of a joint is the body's healing process which fills a joint with fluid. Drains to reduce swelling can help but therapy must start as soon after surgery as possible to minimize formation of scar tissue which can freeze a joint.

Polytetrafluoroethylene (PTFE) is known to be chemically stable and bio-compatible and expanded PTFE has been used in either tubular or sheet form for vascular grafts. In non-medical applications, expanded PTFE is used as a gasket material for example.

As disclosed in U.S. Pat. No. 4,187,390 (Gore), expanded PTFE is typically made by a cold extrusion process in which a paste of PTFE and lubricant is forced through a die. The extruded PTFE expands and is kept expanded during "sintering," i.e. heating the PTFE almost to its melting point, approximately 340° C., and then allowing the PTFE to cool. After sintering, the extrusion is cut into sections and is ready for use. If squeezed between the fingers and released, expanded PTFE compresses and remains in its new shape until extended.

Expanded PTFE has a microscopic structure of nodes interconnected by fibrils and is porous. Porosity is measured as the average distance, e.g. 8–10 microns, from one node to another among a plurality of nodes making up a pore, i.e. porosity is a measure of fibril length. The elastic deformation of millions of tiny fibrils permits the expanded PTFE to compress or stretch and return to its original shape.

In view of the foregoing, it is therefore an object of the invention to provide a joint prosthesis having a longer life in the patient and improved function.

Another object of the invention is to provide a joint prosthesis having a more natural function.

A further object of the invention is to provide a simple joint prosthesis which can move in two axes.

Another object of the invention is to provide a joint prosthesis in which the cushion is preformed with stems for controlling the motion of the joint and enhancing the stability of the joint.

A further object of the invention is to provide a joint prosthesis having high damping capability.

Another object of the invention is to provide a joint prosthesis that is bio-compatible with a patient.

A further object of the invention is to provide a joint prosthesis having controlled adherence to surrounding tissue.

Another object of the invention is to simplify the installation of joint prostheses.

A further object of the invention is to provide a joint prosthesis which cannot fill with body fluids.

Another object of the invention is to provide a prosthesis that is less expensive than prostheses of the prior art while providing the same function.

SUMMARY OF THE INVENTION

The foregoing objects are achieved by the invention in which a mass or cushion of expanded PTFE has at least two facets for attachment between the prepared ends of adjoining bones. In accordance with one aspect of the invention, a portion of the cushion is molded into stems by heating part of the cushion and compressing the PTFE into a low expansion or unexpanded state. In accordance with another aspect of the invention, separate stems are attached to the cushion. In accordance with a third aspect of the invention, a stemless cushion has highly porous facets in contact with the prepared ends of the bones and the bone or fibrous tissue adheres to the porous facets. Since the cushion is porous, a non-porous coating or a thin, non-porous sheath may be added to prevent tissue adherence to the non-facet surfaces of the cushion.

The cushion permits motion along several axes and the orientation of the facets relative to one another affects the motion of the prosthesis. For example, if the facets of the cushion are tilted, i.e. not parallel, then the prosthesis is particularly useful for the MCP joints of the hand which flex further than they hyper-extend. The prosthesis simulates the gliding motion of a natural joint by yielding to shear forces. In accordance with another aspect of the invention, a cushion includes an insert to modify the motion of the prosthesis.

The joint can be installed using current techniques since the stems can be molded in the same shape as stems currently used in other prostheses. Alternatively, a round hole is drilled into the bony canals and round stems are inserted into the holes. Metal sleeves and grommets can be used to separate the PTFE from the bony canal. If a stemless cushion is used, the cushion is inserted between the treated ends of the bones and a cast immobilizes the joint until the bones have had a chance to adhere to the facets of the cushion.

BRIEF DESCRIPTION OF THE DRAWINGS

A more complete understanding of the invention can be obtained by considering the following detailed description in conjunction with the accompanying drawings, in which:

FIGS. 6 and 7 illustrates a prosthetic joint constructed in accordance with the invention;

FIG. 8 illustrates a method for making a prosthetic joint in accordance with the invention;

FIG. 9 illustrate the response of the cushion to shear;

FIG. 10 illustrates a prosthesis constructed in accordance with a preferred embodiment of the invention;

FIG. 11 illustrates the replacement of an MCP joint in a hand;

DETAILED DESCRIPTION OF THE INVENTION

Figure 1:
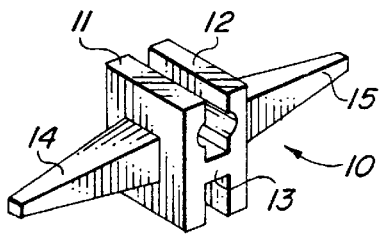
FIGS. 1 and 2 illustrate elastomeric hinges of the prior art.

FIG. 1 illustrates a commercially available, elastomeric, hinge-type prosthesis which includes plates 11 and 12 interconnected by web 13. Stem 14 is attached to plate 11 and stem 15 is attached to plate 12. The stems are inserted directly into the bony canal or are inserted with a metal grommet or metal sleeve to protect the stems from wear by the bone during movement. The stems are non-circular to prevent rotation of prosthesis 10. Up and down motion, as prosthesis 10 is positioned in FIG. 1, is asymmetrical because the web is not centrally located. Web 13 prevents side to side motion.

Figure 2:
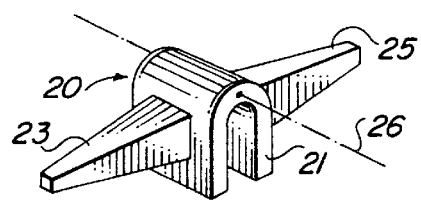

FIG. 2 illustrates a commercially available prosthesis which includes U-shaped elastomeric member 21 having stem 23 attached to one side and stem 25 attached to the other side of member 21. Although the axis of rotation, indicated by reference numeral 26, is displaced from stems 23 and 25, the motion of a joint using prosthesis 20 is nevertheless a hinge-type motion wherein stem 25 rotates about axis 26 relative to stem 23. Prosthesis 20 is capable of considerable rotation as the U is opened.

Figure 3A:
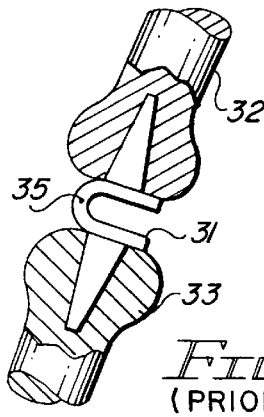
FIGS. 3A and 3B illustrate the movement of a prosthesis having an elastomeric hinge.
Figure 3B:
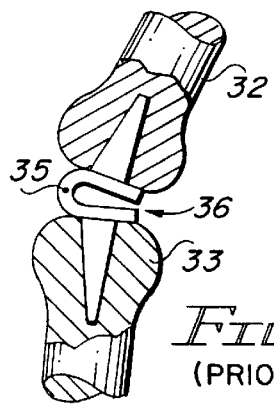

FIG. 3A illustrates prosthesis 31 interconnecting bones 32 and 33. The center of rotation of prosthesis 31 is indicated by reference numeral 35. As shown in FIG. 3B, bone 32 pivots about axis 35 relative to bone 33 moving the ends of the U toward each other at 36. There is no sliding motion, as occurs in natural joints, and the center of rotation is not within either of the bones.

Figure 4A:
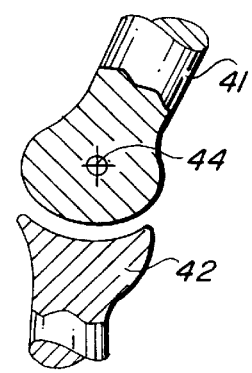
FIGS. 4A, 4B, and 4C illustrate the motion of a natural joint.
Figure 4B:
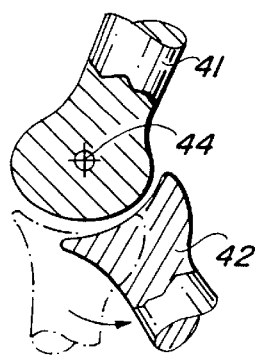

FIG. 4 illustrates the motion of two bones in a natural joint between bone 41 and bone 42. The center of rotation, indicated by reference numeral 44, is within bone 41 away from the end of the bone. This reduces stress on the bones as they move. In FIG. 4B, bone 42 has rotated about axis 44, sliding along the surface contact between the two bones.

Figure 4C:
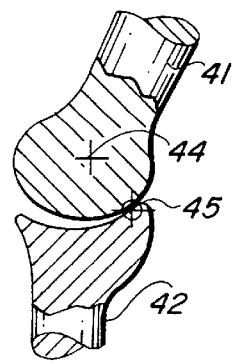

In FIG. 4C, arthritis or other disease can cause the axis of rotation to move from location 44 to a point between the bones indicated by reference numeral 45. When bone 42 can no longer slide across the end of bone 41, bone 42 pivots about point 45 where the forces on the joint are concentrated. This produces great stress on the bone tissue and is extremely painful for a patient.

Figure 5:
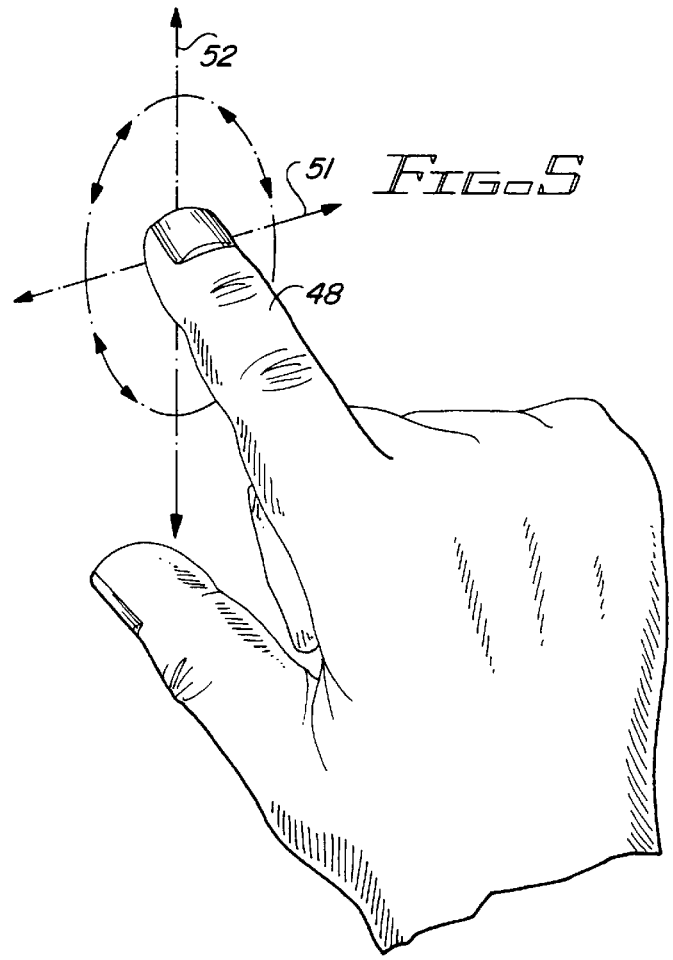
FIG. 5 illustrates the motion of a MCP joint about two axes.

The figures thus far have illustrated the simple motion of a joint about a single axis. FIG. 5 illustrates the motion of an index finger rotating the MCP joint. The tip of index finger 48 traces out an ellipse having X-axis 51 as the minor (shorter) and Y-axis 52 as the major (longer) axis. It is highly desirable to retain this motion for a patient upon replacement of the MCP joint of the index finger.

FIGS. 6 and 7 illustrate a joint constructed in accordance with the invention. Prosthesis 60 includes cushion 61 having stems 62 and 63 extending from opposed facets thereof. Stems 62 and 63 have a non-circular cross-section to accommodate current practice for reconstruction of joints. It is not required by the invention that the stems have any particular cross-section.

Cushion 61 is a mass of expanded PTFE having the approximate consistency of a marshmallow, i.e. it is a highly damped material with little "memory" of a previous shape. Highly damped means that a ball of expanded PTFE would not bounce well, if at all. Cushion 61 can be compressed somewhat and provides progressively greater resistance as it is compressed. It will also stretch slightly if one pulls on the joint. Since cushion 61 is porous, there may be a tendency for the surrounding tissue to adhere to the pores. In order to prevent adherence, cushion 61 may include thin sheath 66 (FIG. 7) of non-porous or low porosity PTFE covering all but the facets. A suitable material for the cushion is Gore-Tex® Joint Sealant as sold by Gore Associates as a gasket material for sealing pipes. A suitable sleeve is similar to vascular graft material, also sold by Gore Associates.

Stems 62 and 63 can be formed as separate elements or, preferably, are integral with cushion 61 and are formed by molding the ends of cushion 61. FIG. 8 illustrates a molding operation in which a cylindrical section of expanded PTFE has the ends thereof inserted into and compressed by heated die 81. Heated die 81 raises the temperature of the expanded PTFE approximately to its melting point, collapsing the material and simultaneously forming stem 62 and facet 68 and stem 63 and facet 69. Facets 68 and 69 are stiff and transmit the forces applied to stems 62 and 63 over the entire cross-section of cushion 61. As indicated in FIG. 7, central region 71 has a lower density (higher porosity) than end regions 72 and 73 and stems 62 and 63.

The motion of prosthesis 60 (FIG. 6) is not a simple rotation about an axis through cushion 61. FIG. 9 illustrates the response of cushion 61 to shear forces. A shear force is a sideward force on an object, such as pushing a stack of coins from one side. As illustrated in FIG. 9, facets 68 and 69 are in parallel planes and cushion 61 is subjected to a shear force, represented by arrow 93. The facets can move past each other while remaining in their parallel planes. While force 93 is illustrated as acting in the plane of the drawing, the joint can respond to a force in a direction perpendicular to the plane of the drawing, or any direction in between. Since the motion in response to shear is combined with a tilting motion, the prosthesis reproduces very closely the motion of a natural MCP joint. As illustrated in FIG. 9, stems 75 and 76 are round.

In FIGS. 6–9, the opposed facets of cushion 61 are illustrated as parallel. For some applications, the facets are preferably tilted with respect to each other, i.e. the facets lie in intersecting planes. FIG. 10 illustrates a preferred embodiment of the invention which is particularly suited to MCP joints which flex more than they hyperextend. As indicated by arrow 101, the upper or outer portion of cushion 102 is wider than the lower or inner portion, as indicated by arrow 103. The tilt between the facets permits bone 104 to move upwardly about cushion 102 relative to bone 105 less than it can move downwardly, as cushion 102 is oriented in FIG. 10. The tilt thus enhances the ability of the reconstructed joint to flex and controls hyper-extension of the reconstructed joint.

Stem 106 is inserted into metal sleeve 107 in bone 105 and stem 108 is inserted into metal sleeve 109 in bone 104. The stems and sleeves have a complementary, non-circular shape to prevent rotation of the cushion.

FIG. 11 illustrates the installation of a prosthesis at the MCP joint of the index finger of a left hand. The diameter of cushion 110, indicated by arrows 111, is determined by the size of a patient's hand, as is the length, indicated by arrows 112. Since the natural joint has a motion of approximately +50°, −90°, the facets of the cushion are not parallel to approximate the same range of movement.

Figure 12A:
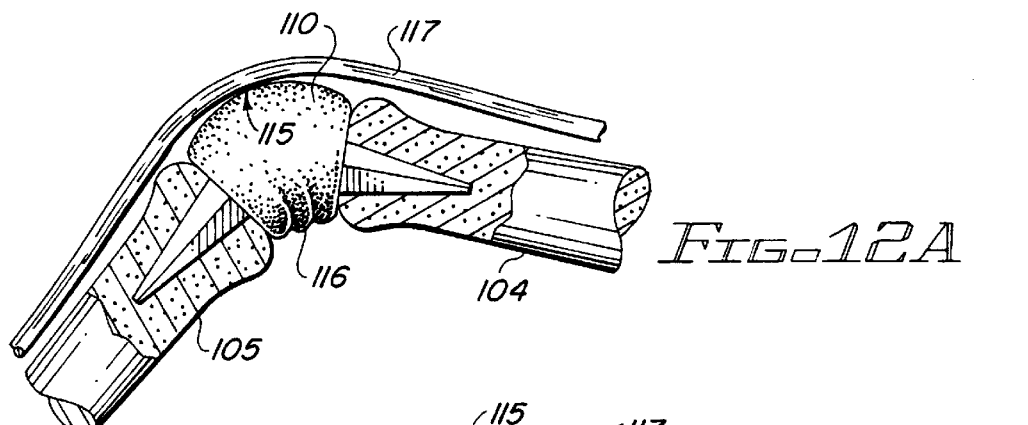
FIGS. 12A and 12B illustrate the motion of a prosthetic joint.
Figure 12B:
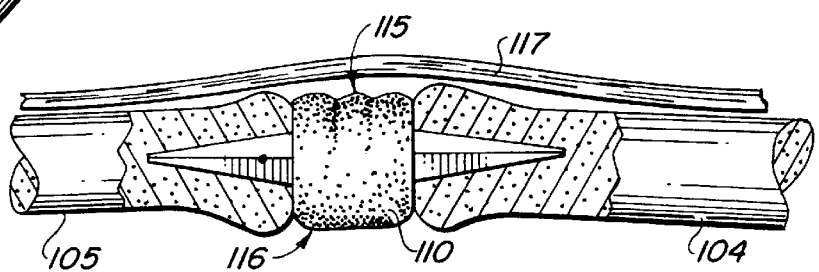

The motion of the prosthesis is illustrated in FIGS. 12A and 12B, which show a combination of shear motion and tilting motion in the cushion. During flexion, outer surface 115 is stretched while inner surface 116 compresses, forming a plurality of folds. Extensor tendon 117 stretches over the prosthesis in a natural curve. Outer surface 115 curves outwardly, giving extensor tendon 117 a better moment arm than obtainable from existing prostheses, making it easier to return the finger to a straight position. In addition, bone 104 moves around bone 105 as if on a sliding joint.

With bones 104 and 105 approximately in a straight line, cushion 110 changes shape as shown in FIG. 12B. Upper surface 115 becomes slightly folded and lower surface 116 becomes smooth. Further extension of bone 104 becomes progressively more difficult because of the greater thickness across the top of cushion 110. Thus, a cushion with non-parallel facets simulates the motion of a natural joint.

Figure 13:
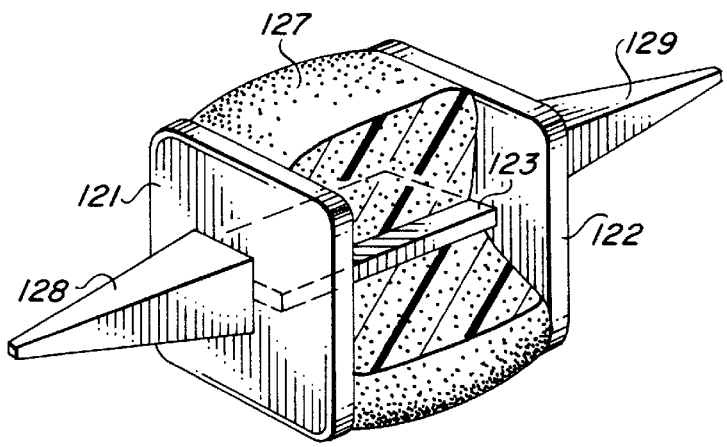
FIG. 13 illustrates a prosthetic joint constructed in accordance with an alternative embodiment of the invention.

The motion of a prosthesis constructed in accordance with the invention can be defined or limited by using non-parallel facets and/or by varying the porosity of the cushion. The motion of the prosthesis can also be controlled by including an insert within the cushion. In FIG. 13 end plates 121 and 122 are connected by flexible web 123. Web 123 has a rectangular cross-section and can bend more freely in an up and down direction than in a direction approximately perpendicular to the plane of the drawing. Cushion 127 surrounds web 123 and provides the resiliency and damping as described in previous embodiments. Web 123 preferably is made from a thin sheet of non-expanded PTFE. In a preferred embodiment of the invention, plates 121 and 122, web 123, and stems 128 and 129 are molded as a single piece from unexpanded PTFE. Expanded PTFE is then extruded about web 123 between plates 121 and 122, forming cushion 127. Alternatively, cushion 127 is slit and inserted about web 123. A non-porous sleeve (not shown) may then be slid over cushion 127, completing the prosthesis. This prosthesis is more suited to the proximal interphlangeal joints of a finger.

Figure 14:
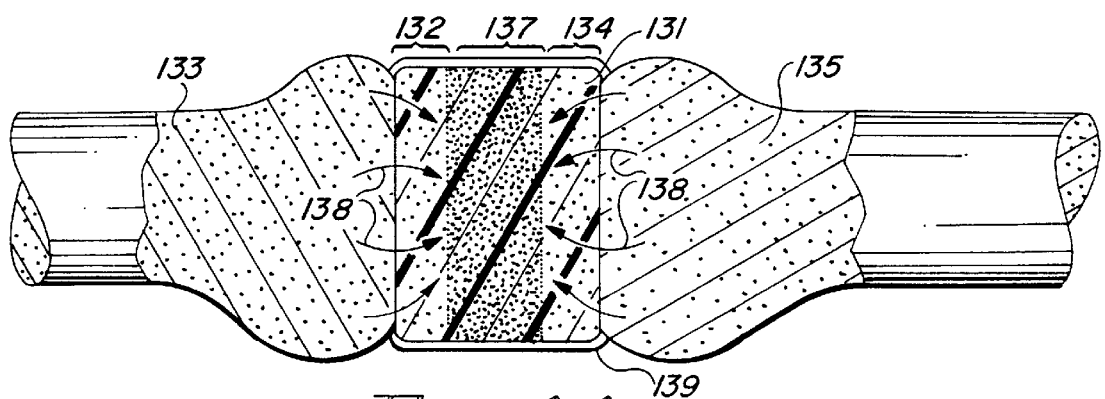
FIG. 14 illustrates a stemless prosthesis constructed in accordance with the invention.

FIG. 14 illustrates an alternative embodiment of the invention wherein no stems are used and the treated ends of the bones are permitted to adhere to the facets of the cushion. Region 132 adjacent bone 133 and region 134, adjacent bone 135, are more porous than central portion 137 of cushion 131. Regions 132 and 134 are more porous to encourage adherence of bone or fibrous tissue, as indicated by arrows 138. Sheath 139 surrounds the outer surface of cushion 131, thereby preventing adherence except at the facets. When this joint is used, the patient's finger is immobilized for a few weeks to permit the adherence of bone or fibrous tissue, just as a broken bone is treated. This joint is more suited to the carpometacarpal (basilar) joint of the thumb.

A joint prosthesis constructed in accordance with the invention is bio-compatible with the patient and should have a long service life. In addition, the prosthesis provides a more natural function than prostheses of the prior art. The inter-nodal distance determines the hardness of the expanded PTFE. Shorter inter-nodal distances produce a relatively hard, low porosity material while larger inter-nodal distances produce a softer, high porosity, high damping material. It has been found that this damping capability is particularly useful in joints since it simulates the natural damping of cartilage between bones.

Having thus described the invention, it will be apparent to those of skill in the art that various modifications can be made within the scope of the invention. For example, the cushion can be any size appropriate for a joint. The porosity of a stemless cushion can be uniform throughout if a highly porous, very soft interface is needed. An insert can be used in any embodiment of the invention. The porosity at which adherence is promoted or prevented may vary with the age of the patient. A porosity greater than six microns is believed to permit adherence of bone or fibrous tissue in adults while a porosity less than six microns is likely to prevent adherence of bone or fibrous tissue.

While described in conjunction with prostheses for a human being, a joint constructed in accordance with the invention can be used on animals or on anatomical models to produce a life-like motion. A joint constructed in accordance with the invention can also be used for joints in robotic "hands" or end effectors where the joints can provide a highly damped, less rigid touch for a robot. Materials other than expanded PTFE can be used provided that they have the same biological and physical properties as described above in connection with expanded PTFE.

What is claimed as the invention is:

1. A joint prosthesis for interconnecting the adjoining ends of metacarpophalangeal bones, said prosthesis comprising:

a cushion of expanded, high-damping polytetrafluoroethylene having a first facet and a second facet, said cushion permitting damped motion between said first facet and said second facet;

a first stem integral with and extending from said first facet for insertion into a hole in the end of a first metacarpophalangeal bone;

a second stem integral with and extending from said second facet for insertion into a hole in the end of a second metacarpophalangeal bone;

wherein said cushion serves to damp motion between said facets, thereby simulating a natural joint between said adjoining ends.

2. The prosthesis as set forth in claim 1 wherein said first facet is parallel to said second facet.

3. The prosthesis as set forth in claim 1 wherein said first facet is tilted with respect to said second facet.

4. A joint prosthesis for replacing a natural joint between a first bone and a second bone which can move relative to the first bone, said prosthesis imitating the motion of the natural joint by interconnecting the adjoining ends of said first bone and said second bone, said prosthesis comprising:

a cushion of expanded, high-damping polytetrafluoroethylene having a first facet and a second facet, said cushion permitting damped motion between said first facet and said second facet;

a first stem integral with and extending from said first facet for attachment to said first bone; and a second stem integral with and extending from said second facet for attachment to said second bone;

wherein said cushion serves to damp motion between said facets, thereby simulating a natural joint between said adjoining ends.

5. The prosthesis as set forth in claim 4 wherein said first stem and said second stem each have a circular cross-section.

* * * * *